United States Patent [19]

Yoshikawa et al.

[11] 4,052,362

[45] Oct. 4, 1977

[54] OLEFIN POLYMER COMPOSITION

[75] Inventors: Toshio Yoshikawa; Nagayoshi Sakamoto; Masayuki Kurita; Shunji Oh-e; Tomitada Nagamori, all of Ichihara, Japan

[73] Assignee: Ube Industries, Ltd., Ube, Japan

[21] Appl. No.: 723,092

[22] Filed: Sept. 14, 1976

[30] Foreign Application Priority Data

Jan. 30, 1976 Japan .................................. 51-8389
May 18, 1976 Japan ................................ 51-56075

[51] Int. Cl.² ............................................. C08K 5/25
[52] U.S. Cl. ...................... 260/45.9 NC; 260/558 H
[58] Field of Search ............... 260/45.9 NC, 45.85 B; 174/23 C

[56] References Cited

U.S. PATENT DOCUMENTS 3,773,722  11/1973  Dexter .................. 260/45.9 NC
3,806,358  4/1974  Clander et al. .......... 260/45.9 NC

*Primary Examiner*—V. P. Hoke
*Attorney, Agent, or Firm*—Flynn & Frishauf

[57] ABSTRACT

A stabilized olefin polymer composition having resistance against deterioration caused by contact with such heavy metals as copper which comprises 100 parts by weight of an olefin polymer and from 0.001 to 5 parts by weight of an N-cinnamoyl-N'-acyl-hydrazine derivative is disclosed.

12 Claims, No Drawings

OLEFIN POLYMER COMPOSITION

This invention relates to an olefin polymer composition having resistance against deterioration caused by contact with heavy metals.

Heretofore, such olefin polymers as polyethylene, polypropylene, and polybutene have been employed over a wide range of uses owing to their excellent physical or chemical characteristics. However, as is commonly known, if an olefin polymer is employed with no additives, it will deteriorate under the influence of heat, light or oxygen during processing or use. In order to prevent such deterioration, several kinds of anti-oxidizing agents have been studied and employed.

Yet, where olefin polymers cannot be kept from contact with such heavy metals as copper, iron, and nickel, for instance, when covering copper wire with olefin polymers, plating olefin polymers with heavy metals, or coloring olefin polymers by pigments containing heavy metals, the use of the aforementioned conventional anti-oxidizing agents can hardly bring about resistance against deterioration caused by contact with heavy metals.

Further, if liquid amorphous olefin polymers may possibly come into contact with copper, for instance, if a liquid amorphous olefin polymer is employed as an insulating oil for cable, resistance against deterioration caused by contact with copper is required. Yet, the mere use of the aforementioned conventional anti-oxidizing agents cannot meet the above-mentioned requirement.

For the above reasons, a number of compounds were presented to use as the anti-deteriorating agents for imparting olefin polymers the resistance against deterioration caused by contact with heavy metals. Such compounds are mentioned as follows: N,N'-dibenzoylhydrazine, N-benzoyl-N'-salicyloylhydrazine, N,N'-dibutyrylhydrazine, N,N'-distearoylhydrazine, N,N'-bis[-(3,5-di-tert-butyl-4-hydroxyphenyl)propionyl]hydrazine, N,N'-bissalicyloylhydrazine, oxalobis(benzylidenehydrazide), N-salicylidene-N'-salicyloylhydrazine, etc. Yet, these agents cannot be considered agents satisfying the requirement of providing an anti-deteriorating effect.

This invention provides an olefin polymer composition having resistance against deterioration caused by contact with heavy metals which comprises 100 parts by weight of an olefin polymer and from 0.001 to 5 parts by weight of a compound having the formula (I)

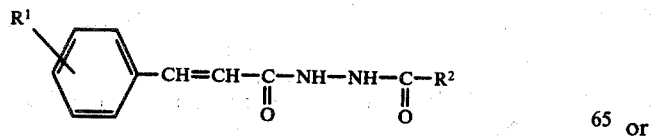

in which $R^1$ represents a hydrogen atom, a halogen atom, a hydroxyl group, an alkyl group having 1 − 3 carbon atoms or an alkoxy group having 1 − 3 carbon atoms, and $R^2$ represents a group of the formula

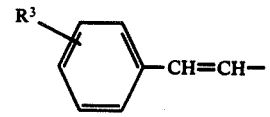

in which $R^3$ represents a hydrogen atom, a hydroxyl group, an alkyl group having 1 − 3 carbon atoms or an alkoxy group having 1 − 3 carbon atoms, a group of the formula

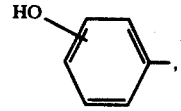

a group of the formula

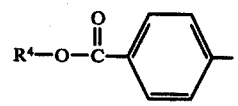

in which $R^4$ represents an alkyl group having 1 − 3 carbon atoms, or a group of the formula

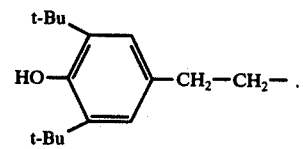

Olefin polymers of the composition of the present invention may be exemplified by amorphous or crystalline homopolymers or copolymers of such olefins as ethylene, propylene, butene-1, isobutene, pentene-1 and 4-methylpentene-1; copolymers of these olefins and alkyl esters of unsaturated carboxylic acids, e.g., methyl acrylate, ethyl acrylate, methyl methacrylate and ethyl methacrylate; copolymers of these olefins and such vinyl esters of saturated carboxylic acids as vinyl acetate; mixtures of these polymers; liquid amorphous polypropylene; and liquid amorphous polybutene.

The compound of the formula (I), which acts as an antideteriorating agent in the composition, can be easily prepared, for instance, by the following reactions.

A. Compounds of the formula (I) in which $R^2$ is one of the groups of the formulae;

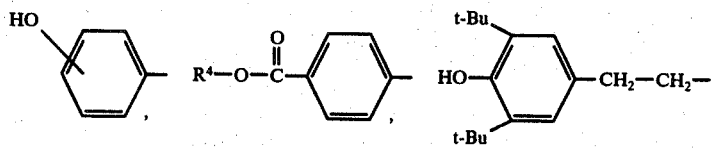

$$R^5COOR^6 + NH_2NH_2 \rightarrow R^5CONHNH_2 + R^6OH \quad (1)$$

$$R^5CONHNH_2 + R^5COCl \rightarrow R^2CONHNHCOR^2 + HCl \quad (2)$$

or $$R^2COOR^6 + NH_2NH_2 \rightarrow R^2CONHNH_2 + R^6OH \quad (3)$$

$R^2CONHNH_2 + R^5COCl \rightarrow R^2CONHNHCOR^5 +$ HCl　　　(4)

(In the above, $R^5$ is a group of the formula

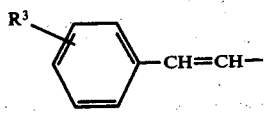

and $R^6$ is an alkyl group.)

B. Compounds of the formula (I) in which $R^2$ is a group of the formula

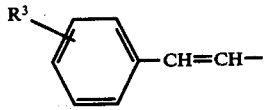

(in other words, the above $R^5$)

$2R^2COCl + NH_2NH_2 \rightarrow R^2CONHNHCOR^2 + 2HCl$　　　(5)

In the above-illustrated reactions, the hydrazine can be likewise conveniently employed in the form of hydrazine hydrate, hydrazine sulfate, hydrazine hydrochloride or one of other hydrazine adducts. When hydrazine sulfate or hydrazine hydrochloride is employed, however, it is required that such an alkaline compound as sodium hydroxide, potassium hydroxide, sodium carbonate, potassium carbonate, sodium hydrogencarbonate or potassium hydrogencarbonate is incorporated into the reaction mixture to produce free hydrazine.

The reactions of the above-mentioned (1) and (3) readily proceed in the presence or absence of such a lower alcohol as methyl alcohol or ethyl alcohol when the reaction mixture is kept at a temperature of above 20° C. The reactions of the above-mentioned (2), (4) and (5) readily proceed in the presence or absence of such a solvent as N-dimethylacetamide, methylformamide, benzene, toluene, xylene, chloroform, ethyl acetate, dichlorobenzene, methylene chloride, carbon tetrachloride or tetrahydrofuran when the reaction mixture is kept at a temperature in the range of from 0° to 100° C, preferably from 20° to 60° C.

The compounds of the formula (I) produced in the reactions are isolated from the reaction mixture after the reaction is completed. Examples of the procedures are described in the following. After completion of the reaction, the reaction mixture is poured into a large amount of water, and the produced precipitate is collected by filtration. The precipitate is then washed with water and recrystallized from a recrystallization solvent such as a lower alcohol, e.g., methanol or ethanol, an aqueous lower alcohol, a lower aliphatic acid, e.g., acetic acid or propionic acid, an aqueous lower aliphatic acid, an N-dialkylacid amide, e.g., N-dimethylacetamide or dimethylformamide, an aqueous N-dialkylacid amide, or a hydrocarbon, e.g., benzene, toluene or n-hexane.

In view of the anti-deteriorating effect and other factors, the following compounds are preferably employed in the present composition.

Compounds having the formula (II)

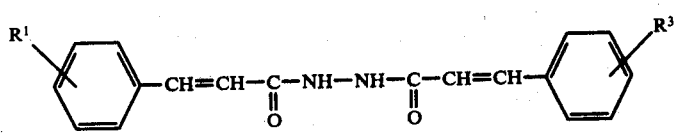

in which $R^1$ represents a hydrogen atom, a halogen atom, an alkyl group having 1 – 3 carbon atoms or an alkoxy group having 1 – 3 carbon atoms, and $R^3$ represents a hydrogen atom, an alkyl group having 1 – 3 carbon atoms or an alkoxy group having 1 – 3 carbon atoms.

Compounds having the formula (III)

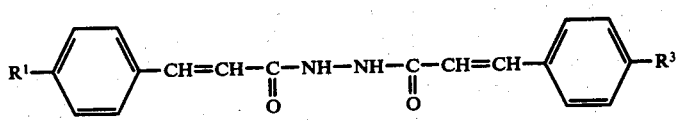

in which $R^1$ and $R^3$ may be the same or different, and each represents a hydrogen atom, or a methyl or methoxy group.

Compounds having the formula (IV)

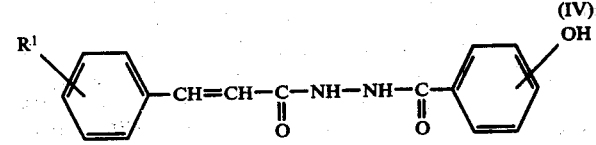

in which $R^1$ represents a hydrogen atom, a halogen atom, an alkyl group having 1 – 3 carbon atoms or an alkoxy group having 1 – 3 carbon atoms.

Compounds having the formula (V)

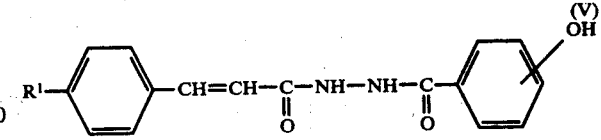

in which $R^1$ represents a hydrogen atom, or a methyl or methoxy group.

Compounds having the formula (VI)

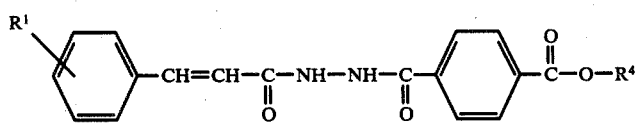
(VI)

in which R¹ represents a hydrogen atom, a halogen atom, an alkyl group having 1 - 3 carbon atoms or an alkoxy group having 1 - 3 carbon atoms, and R⁴ represents an alkyl group having 1 - 3 carbon atoms.

Compounds having the formula (VII)

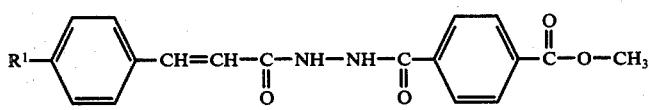
(VII)

in which R¹ has the same meaning as that for the formula (V).

Compounds having the formula (VIII)

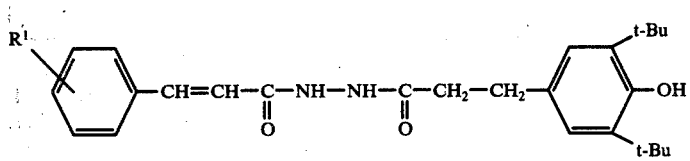
(VIII)

in which R¹ has the same meaning as that for the formula (VI).

Compounds having the formula (IX)

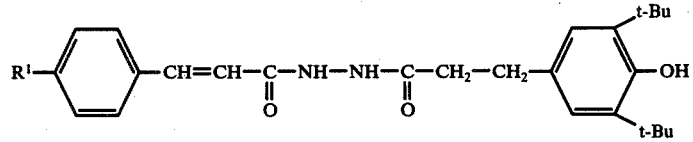
(IX)

in which R¹ represents a hydrogen or chlorine atom or a methyl or methoxy group.

Compounds preferably used in the composition of the present invention may be exemplified as follows: N,N'-biscinnamoylhydrazine, N-cinnamoyl-N'-(p-methoxycinnamoyl)hydrazine, N-cinnamoyl-N'-(p-methylcinnamoyl)hydrazine, N,N'-bis(p-methoxycinnamoyl)hydrazine, N,N'-bis(p-methylcinnamoyl)hydrazine, N-cinnamoyl-N'-(p-hydroxybenzoyl)hydrazine, N-cinnamoyl-N'-salicyloylhydrazine, N-cinnamoyl-N'-(p-methoxycarbonylbenzoyl)hydrazine, N-(p-methoxycinnamoyl)-N'-salicyloylhydrazine, N-(p-methylcinnamoyl)-N'-salicyloylhydrazine, N,N'-bis(p-ethylcinnamoyl)hydrazine, N,N'-bis(p-propylcinnamoyl)hydrazine, N-(p-methylcinnamoyl)-N'-(p-ethylcinnamoyl)hydrazine, N-(p-methylcinnamoyl)-N'-(p-methoxycinnamoyl)hydrazine, N-(p-methylcinnamoyl)-N'-(p-ethoxycinnamoyl)hydrazine, N-(p-methylcinnamoyl)-N'-(p-methoxycarbonylbenzoyl)hydrazine, N-(p-ethylcinnamonyl)-N'-(p-methoxycarbonylbenzoyl)hydrazine, N-(p-propylcinnamoyl)-N'-(p-methoxycarbonylbenzoyl)hydrazine, N-(p-methoxycinnamoyl)-N'-(p-methoxycarbonylbenzoyl)hydrazine, N-(p-ethoxycinnamoyl)-N'-(p-methoxycarbonylbenzoyl)hydrazine, N-(p-propoxycinnamoyl)-N'-(p-methoxycarbonylbenzoyl)hydrazine, N-cinnamoyl-N'-{β-(3,5-di-tert-butyl-4-hydroxyphenyl)propionyl}-hydrazine, N-(p-methylcinnamoyl)-N'-{β-(3,5-di-tert-butyl-4-hydroxyphenyl)-propionyl}hydrazine, N-(p-methoxycinnamoyl)-N'-{β-(3,5-di-tert-butyl-4-hydroxyphenyl)propionyl}hydrazine, and N-(p-chlorocinnamoyl)-N'-{β-(3,5-di-tert-butyl-4-hydroxyphenyl)propionyl}hydrazine.

In the composition of the present invention, the amount of the anti-deteriorating agent of the formula (I) is from 0.001 to 5 parts by weight, preferably from 0.01 to 3 parts by weight per 100 parts by weight of olefin polymers. An amount less than the above-mentioned 0.001 part by weight cannot bring about a sufficient anti-deteriorating effect, and an amount of more than 5 parts by weight cannot provide any further anti-deteriorating effect.

Any process suitable for preparation of a homogeneous composition may be adopted for mixing or compounding the aforesaid anti-deteriorating agent with the olefin polymer, for example, dissolving or dispersing the anti-deteriorating agent in a low-boiling solvent, mixing the solution within olefin polymer and removing the solvent by evaporation; heating an olefin polymer above its melting point on a surface of a heated roller and then mixing the anti-deteriorating agent therewith; or mixing an olefin polymer with the anti-deteriorating agent by means of a conventional mixer.

In addition, the anti-deteriorating agent of the formula (I) used in the present invention may be employed together with stabilizing agents, dispersing agents, plasticizers, antistatic agents, fillers, pigments, and/or other conventional additives.

The stabilizing agents may be exemplified by phenol-type compounds, for instance, 2,6-di-tert-butyl-p-cresol, 2,6-di-tert-butylphenol, 4,4'-methylenebis(2,6-di-tert-butylphenol), 4,4'-methylenebis(3-methyl-6-tert-butylphenol), 4,4'-thiobis(2,6-di-tert-butylphenol), 4,4'-thiobis(2-methyl-6-tert-butylphenol), 6-(4-hydroxy-3,5-di-tert-butylanilino)-2,4-bis(n-octylthio)-1,3,5-triazine, tetrakis[methylene 3-(3,5-di-tert-butyl-4-hydroxyphenyl)-propionate]-methane, octadecyl 3-(3,5-di-tert-butyl-4-hydroxyphenyl)propionate, 1,1,3-tris(2-methyl-4-hydroxy-5-tert-butylphenyl)butane, 2,2'-methylenebis(4-methyl-6-tert-butylphenol),4,4'-butylidenebis(3-methyl-6-tert-butylphenol), 2,2'-methylenebis(4-ethyl-6-tert-butylphenol), and 1,3,5-trimethyl-2,4,6-tris(3,5-di-tert-butyl-4-hydroxybenzyl)-benzene; dialkyl 3,3'-thiodiporpionates, for instance, didodecyl 3,3'-thiodipropionate and dioctadecyl 3,3'-thiodipropionate; and organic phosphorus compounds, for instance, trilauryl phosphite, trilauryl trithiophosphite and tris(nonylphenyl) phosphite.

Synthesis examples of the compound of the formula (I) which acts as the anti-deteriorating agent in the composition of the present invention will be illustrated below.

SYNTHESIS EXAMPLE 1 SYNTHESIS OF N,N'-BISCINNAMOYLHYDRAZINE

A solution of 9.5 g of hydrazine sulfate and 8.0 g of sodium hydroxide in 83 ml of water was stirred at 20° –30° C while cooled with ice. To the resulting solution were slowly added dropwise 25 g of cinnamoyl chloride and 7.5 g of sodium hydroxide in 20 ml of water. After completion of the addition, the mixture was stirred at 20° –30° C for 2 hours. The produced precipitate was collected by filtration and washed with water. The so obtained product was then recrystallized twice from acetic acid (first grade, prepared and sold by Wako Junyaku Kabushiki Kaisha, Japan, the same in the following) and dried under reduced pressure to yield 11.6 g of N,N'-biscinnamoylhydrazine as white needles, m.p. 267° – 268° C. Analysis: Calculated for $C_{18}H_{16}N_2O_2$: C, 73.97%; H, 5.48%, N, 9.5%, Found: C, 74.17%; H, 5.55%; N, 9.69%.

SYNTHESIS EXAMPLE 2 SYNTHESIS OF N-CINNAMOYL-N'-(P-METHOXYCINNAMOYL)HYDRAZINE

In a flask equipped with a reflux condenser were placed 5.0 g of p-methoxy cinnamic acid and 15 g of thionyl chloride, and the reaction was carried out under reflux. After evolvement of hydrogen chloride and sulfur dioxide ceased, the residual thionyl chloride was distilled off under reduced pressure. To the remaining p-methoxycinnamoyl chloride was added 4.6 g of cnnamoylhydrazine, and the reaction was carried out with stirring at 70° –80° C for 5 hours. The reaction mixture was then poured into 10% aqueous sodium hydroxide, and the produced precipitate was collected by filtration and washed with water. The so obtained product was then recrystallized twice from acetic acid and dried under reduced pressure to yield 4.6 g of N-cinnamoyl-N'-(p-methoxycinnamoyl)hydrazine as white needles, m.p. 263° C. Analysis: Calculated for $C_{19}H_{18}N_2O_3$: C, 70.81%; H, 5.59%; N, 8.70%, Found: C, 71.15%; H, 5.43%; N, 8.65%.

SYNTHESIS EXAMPLE 3 SYNTHESIS OF N,N'-BIS(P-METHOXYCINNAMOYL)-HYDRAZINE

The procedure of Synthesis example 2 was repeated except that 10 g of p-methoxycinnamic acid and 40 g of thionyl chloride were employed and that 1.5 g of 90% hydrazine hydrate was employed in place of the cinnamoylhydrazine. There was obtained 7 g of N,N'-bis(p-methoxycinnamoyl)hydrazine as white needles, m.p. 288° C. Analysis: Calculated for $C_{20}H_{20}N_2O_4$: C, 68.18%; H, 5.68%; N, 7.95%, Found: C, 68.20%; H, 5.64%; N, 7.81%.

SYNTHESIS EXAMPLE 4 SYNTHESIS OF N-CINNAMOYL-N'-SALICYLOYLHYDRAZINE

To 50 ml of N-dimethylacetamide were added 5.0 g of salicyloylhydrazine and 5.5 g of cinnamoyl chloride, and the mixture was stirred at 20° C for 9 hours. The reaction mixture was then poured into 2 liters of water, and the produced precipitate was collected by filtration and washed with water. The so obtained product was then recrystallized twice from acetic acid and dried under reduced pressure to yield 3 g of N-cinnamoyl-N'-salicyloylhydrazine as white crystals, m.p. 271° C. Analysis: Calculated for $C_{16}H_{14}N_2O_3$; C, 68.09%, H, 4.96%; N, 9.93%, Found: C, 68.08%; H, 4.81%; N, 9.08%.

SYNTHESIS EXAMPLE 5 SYNTHESIS OF N-CINNAMOYL-N'-(P-HYDROXYBENZOYL)HYDRAZINE

To 100 ml of acetic acid were added 5.0 g of p-hydroxybenzoylhydrazine and 5.5 g of cinnamoyl chloride, and the mixture was stirred at 20° C for 3 hours. The reaction mixture was then poured into 2 liters of water, and the produced precipitate was collected and washed with water. The so obtained product was then recrystallized twice from acetic acid and dried under reduced pressure to yield 3.1 g of N-cinnamoyl-N'-(p-hydroxybenzoyl)hydrazine as white crystals, m.p. 263°–264.5° C. Analysis: Calculated for $C_{16}H_{14}N_2O_3$: C, 68.08%; H, 5.00 %; N, 9.92%, Found: C, 68.15%; H, 4.87%; N, 9.98%.

SYNTHESIS EXAMPLE 6 SYNTHESIS OF N,N'-BIS(P-METHYLCINNAMOYL)HYDRAZINE

In a flask were placed 10 g of p-methylcinnamic acid and 25 g of thionyl chloride, and the mixture was heated until evolvement of hydrogen chloride and sulfur dioxide ceased. After the heating, the residual thionyl chloride was distilled off under reduced pressure. To the remaining p-methylcinnamoyl chloride was slowly added dropwise 1.8 g of 85% hydrazine hydrate, and the reaction was carried out at 20° – 30° C for about 3 hours. The reaction mixture was then poured into 10% aqueous sodium hydroxide, and the produced precipitate was collected by filtration and washed with water. The so obtained product was then recrystallized twice from acetic acid and dried under reduced pressure to yield 7.5 g of N,N'-bis(p-methylcinnamoyl)-hydrazine as white crystals, m.p. 307° C. Analysis: Calculated for $C_{20}H_{20}N_2O_2$ : C, 75.00%; H, 6.25%; N, 8.75%, Found: C, 75.32%; H, 6.18%; N, 8.75%.

SYNTHESIS EXAMPLE 7 SYNTHESIS OF N-CINNAMOYL-N'-(P-METHOXYCARBONYL-BENZOYL)HYDRAZINE

In a flask were placed 5 g of p-methoxycarbonylbenzoylhydrazine, 4.3 g of cinnamoyl chloride and 30 ml of N-dimethylacetamide, and the reaction was carried out with stirring at 30° – 40° C for 6 hours. After completion of the reaction, the produced precipitate was collected by filtration and washed with water. The so obtained precipitate was then recrystallized twice from acetic acid and dried under reduced pressure to yield 6 g of N-cinnamoyl-N'-(p-methoxycarbonylbenzoyl)hydrazine as white crystals, m.p. 207° C. Analysis: Calculated for $C_{18}H_{16}N_2O_4$: C, 66.67%; H, 4.94%; N, 8.64%, Found: C, 66.51%; H, 4.98%; N, 8.71%.

SYNTHESIS EXAMPLE 8 SYNTHESIS OF N-CINNAMOYL-N'-{β-(3,5-DI-TERT-BUTYL-4-HYDROXYPHENYL)PROPIONYL} HYDRAZINE

To 50 ml of N-dimethylacetamide were added 2.30 g of cinnamoyl chloride and 4.04 g of β-(3,5-di-tert-butyl-4-hydroxyphenyl)propionylhydrazine, and the resulting mixture was stirred at 30° – 35° C for 3 hours. The reaction mixture was then poured into 2 liters of water, and the produced precipitate was collected by filtration and washed with water. The so obtained precipitate was then recrystallized twice from a mixture of ethanol (first grade) and water (1 : 1, volume ratio) and dried under reduced pressure to yield 4.1 g of N-cinnamoyl-N'-{β-(3,5-di-tert-butyl-4-hydroxyphenyl)propionyl}-hydrazine as white crystals, m.p. 224.5° – 225.0° C. Analysis for $C_{26}H_{34}N_2O_8$: C, 73.90%, H, 8.11%; N, 6.63%, Found: C, 73.91%; H, 7.90%; N, 6.51%.

SYNTHESIS EXAMPLE 9 SYNTHESIS OF N-(P-METHYLCINNAMOYL)-N'-{β-(3,5-DI-TERT-BUTYL-4-HYDROXYPEHNYL)PROPIONYL}HYDRAZINE

In a flask equipped with a reflux condenser were placed 16.22 g of p-methylcinnamic acid and 23.80 g of thionyl chloride, and the reaction was carried out under reflux. After evolvement of hydrogen chloride and sulfur dioxide ceased, the residual thionyl chloride was distilled off under reduced pressure. The remaining p-methylcinnamoyl chloride was dissolved in 100 ml of ethyl acetate, and this solution was slowly added dropwise with stirring to a solution of 29.24 g of β-(3,5-di-tert-butyl-4-hydroxyphenyl)propionylhydrazine in 200 ml of ethyl acetate. After the addition was completed, the mixture was stirred at 20° – 30° C for 5 hours. The produced precipitate was collected by filtration and washed successively with 10% (by weight) aqueous sodium hydrogencarbonate, 10% (by weight) hydrochloric acid and water. The so obtained product was then recrystallized twice from a mixture of ethanol (first grade) and water (1 : 1, volume ratio) and dried under reduced pressure to yield 27 g of N-(p-methylcinnamoyl)-N'-{β-(3,5-di-tert-butyl-4-hydroxyphenyl)propionyl}hydrazine as white crystals, m.p. 274.0° – 275.0° C. Analysis: Calculated for $C_{27}H_{36}N_2O_3$: C, 74.28%; H, 8.31%; N, 6.42%, Found: C, 74.08%; H, 8.13%; N, 6.42%.

SYNTHESIS EXAMPLE 10 SYNTHESIS OF N-(P-METHOXYCINNAMOYL)-N'-{β-(3,5-DI-TERT-BUTYL-4-HYDROXYPHENYL)PROPIONYL}HYDRAZINE

The procedure of Synthesis example 9 was repeated except for replacing 16.22 g of p-methylcinnamic acid by 17.82 g of p-methoxycinnamic acid to obtain a product. The so obtained product was recrystallized twice from a mixture of ethanol (first grade) and water (1 : 1, volume ratio) and dried under reduced pressure to yield 16.5 g of N-(p-methoxycinnamoyl)-N'-{β-(3,5-di-tert-butyl-4-hydroxyphenyl)propionyl}hydrazine as white crystals, m.p. 252.0° – 253.5° C. Analysis: Calculated for $C_{27}H_{36}N_2O_4$: C, 71.65%; H, 8.02%; N, 6.19%, Found: C, 71.48%; H, 8.01%; N, 6.08%.

SYNTHESIS EXAMPLE 11 SYNTHESIS OF N-(P-CHLOROCINNAMOYL)-N'-{β-(3,5-DI-TERT-BUTYL-4-HYDROXYPHENYL)PROPIONYL}HYDRAZINE

The procedure of Synthesis example 9 was repeated except for replacing 16.22 g of p-methylcinnamic acid by 18.26 g of p-chlorocinnamic acid to obtain a product. The so obtained product was recrystallized twice from a mixture of ethanol (first grade) and water (1 : 1, volume ratio) and dried under reduced pressure to yield 13 g of N-(p-chlorocinnamoyl)-N'-{β-(3,5-di-tert-butyl-4-hydroxyphenyl)propionyl}hydrazine as white crystals, m.p. 276.0° – 277.0° C. Analysis: Calculated for $C_{26}H_{33}ClN_2O_3$: C, 68.33%; H, 7.28%; Cl, 7.76%; N, 6.13%, Found: C, 68.51%; H, 7.34%; Cl, 7.54%; N, 6.03%.

The following are examples and comparative examples. The term "part" means "part by weight", and "M.I." means "Melt Flow Index" which was determined in accordance with ASTMD 1238. The notations shown in the examples and comparative examples mean the following compounds.

A: N,N'-biscinnamoylhydrazine
B: N-cinnamoyl-N'-(p-methoxycinnamoyl)hydrazine
C: N,N'-bis(p-methoxycinnamoyl)hydrazine
D: N-cinnamoyl-N'-salicyloylhydrazine
E: N-cinnamoyl-N'-(p-hydroxybenzoyl)hydrazine
F: N,N'-bis(p-methylcinnamoyl)hydrazine
G: N-cinnamoyl-N'-(p-methoxycarbonylbenzoyl)hydrazine
H: N-cinnamoyl-N'-{β-(3,5-di-tert-butyl-4-hydroxyphenyl)propionyl}hydrazine
I: N-(p-methylcinnamoyl)-N'-{β-(3,5-di-tert-butyl-4-hydroxyphenyl)propionyl}hydrazine
J: N-(p-methoxycinnamoyl)-N'-{β-(3,5-di-tert-butyl-4-hydroxyphenyl)propionyl}hydrazine
K: N-(p-chlorocinnamoyl)-N'-{β-(3,5-di-tert-butyl-4-hydroxyphenyl)propionyl}hydrazine
a: N,N'-dibenzoylhydrazine
b: N-benzoyl-N'-salicyloylhydrazine
c: N,N'-dibutyrylhydrazine
d: N,N'-distearoylhydrazine
e: N,N'-bis{β-(3,5-di-tert-butyl-4-hydroxyphenyl)propionyl}-hydrazine
f: N,N'-bissalicyloylhydrazine
g: N-salicyloyl-N'-stearoylhydrazine
h: N,N'-bis(p-methylbenzoyl)hydrazine
i: N,N'-bis(p-methoxybenzoyl)hydrazine
j: N,N'-bis(p-acetoxybenzoyl)hydrazine
k: oxalobis(benzylidenehydrazide)
l: N-salicylidene-N'-salicyloylhydrazine
m: N-stearoyl-N'-{β-(3,5-di-tert-butyl-4-hydroxyphenyl)propionyl}hydrazine
n: β-(3,5-di-tert-butyl-4-hydroxyphenyl)propionylhydrazine
o: N,N'-dicrotonoylhydrazine
p: N-salicyloyl-N'-(p-methylbenzoyl)hydrazine
q: N-salicyloyl-N'-(p-methoxybenzoyl)hydrazine The compounds a – q are conventional andi-deteriorating agents.

EXAMPLES 1 – 11

One hundred parts of powdery isotactic polypropylene with no additives (M.I. = 5), 0.2 part of tetrakis[methylene 3-(3,5-di-tert-butyl-4-hydroxyphenyl)propionate]methane, 0.5 part of distearyl 3,3'-thiodipropionate, 1.0 part of 2.6-di-tert-butyl-p-cresol and 0.2 part of a compound set out in Table 1 were preliminarily mixed in a mixer. This mixture was placed in a Brabender plastograph adjusted to a rotation speed of 60 r.p.m. and a temperature of 190° C, and kneaded for 5 minutes. The resulting mixture was pressed at 190° C by the use of a spacer to form a film having thickness of 0.5 mm. Between a couple of the so obtained films was placed a copper net of 60 meshes, and this was then pressed at 190° C by the use of a spacer of thickness of 0.8 mm to obtain a copper net buried film. The so obtained film was cut into rectangular (50 mm × 30 mm) pieces which were in turn subjected to the test described below.

The test pieces were suspended in a Geer's oven under an aerial atmosphere at 150° C, and the period at the end of which the pieces deteriorated were determined. The results are set forth in Table 1.

Table 1

| Example No. | Compound added | Period up to deterioration (days) |
| --- | --- | --- |
| 1 | A | 95 |
| 2 | B | 84 |
| 3 | C | 82 |
| 4 | D | 89 |
| 5 | E | 84 |
| 6 | F | 92 |
| 7 | G | 89 |
| 8 | H | 94 |
| 9 | I | 90 |
| 10 | J | 92 |
| 11 | K | 85 |

COMPARATIVE EXAMPLES 1 – 18

The procedures of Examples 1 – 11 were repeated except that conventional anti-deteriorating agents $a - q$ were employed in place of the compounds A – K. In Comparative example 1, no anti-deteriorating agent was added. The results are set forth in Table 2.

Table 2

| Comparative example No. | Anti-deteriorating agent | Period up to deterioration (days) |
| --- | --- | --- |
| 1 | — | 1 |
| 2 | a | 11 |
| 3 | b | 18 |
| 4 | c | 7 |
| 5 | d | 5 |
| 6 | e | 31 |
| 7 | f | 15 |
| 8 | g | 13 |
| 9 | h | 9 |
| 10 | i | 8 |
| 11 | j | 11 |
| 12 | k | 25 |
| 13 | l | 27 |
| 14 | m | 12 |
| 15 | n | 15 |
| 16 | o | 5 |
| 17 | p | 15 |
| 18 | q | 16 |

EXAMPLES 12 – 22

One hundred parts of pellets of high-density polyethylene with no additives (M.I. = 0.30) were placed in a Brabender plastograph adjusted to a rotation speed of 60 r.p.m. and a temperature of 190° C. Two minutes later, 0.15 part of tetrakis[methylene 3-(3,5-di-tert-butyl-4-hydroxyphenyl)propionate]methane and 0.2 part of a compound set out in Table 3 were added thereto, and the mixture was then kneaded for 6 minutes. This was pressed at 190° C by the use of a spacer to form a film having thickness of 0.5 mm. Between a couple of the so obtained films was placed a copper net of 60 meshes, and this was then pressed at 190° C by the use of a spacer of thickness of 0.8 mm to obtain a copper net buried film. The so obtained film was cut into rectangular (10 mm × 5 mm) pieces which were in turn subjected to the test described below.

The test pieces were examined by Oxygen Absorption Method. The pieces were heated to 170° C under an oxygenic atmosphere, and the relation between an amount of the absorbed oxygen and a period of time was checked. The period in minutes at the end of which the absorbed oxygen amounted to 5 ml (20° C, at an atmospheric pressure) per one gram of the piece was determined. This period is called "Induction period", and the results are set forth in Table 3.

Table 3

| Example No. | Compound added | Induction period (minutes) |
| --- | --- | --- |
| 12 | A | 2180 |
| 13 | B | 1990 |
| 14 | C | 1970 |
| 15 | D | 2040 |
| 16 | E | 2000 |
| 17 | F | 2000 |
| 18 | G | 1960 |
| 19 | H | 2100 |
| 20 | I | 2000 |
| 21 | J | 2050 |
| 22 | K | 1910 |

COMPARATIVE EXAMPLES 19 – 36

The procedures of Examples 12 – 22 were repeated except that conventional anti-deteriorating agents $a - q$ were employed in place of the compounds A – K. In comparative example 19, no anti-deteriorating agent was added. The results are set forth in Table 4.

Table 4

| Comparative example No. | Anti-deteriorating agent | Induction period (minutes) |
| --- | --- | --- |
| 19 | — | 135 |
| 20 | a | 430 |
| 21 | b | 520 |
| 22 | c | 350 |
| 23 | d | 320 |
| 24 | e | 750 |
| 25 | f | 480 |
| 26 | g | 410 |
| 27 | h | 420 |
| 28 | i | 380 |
| 29 | j | 390 |
| 30 | k | 715 |
| 31 | l | 700 |
| 32 | m | 380 |
| 33 | n | 420 |
| 34 | o | 300 |
| 35 | p | 420 |
| 36 | q | 450 |

EXAMPLES 23 – 33

The procedures of Examples 12 – 22 were repeated except that the high-density polyethylene was replaced by a low-density polyethylene (M.I. = 0.25) and that the temperature of the kneading (the temperature of the Brabender plastograph) was changed into 140° C. The Induction periods are set forth in Table 5.

Table 5

| Example No. | Compound added | Induction period (minutes) |
| --- | --- | --- |
| 23 | A | 1990 |
| 24 | B | 1870 |
| 25 | C | 1840 |
| 26 | D | 1900 |
| 27 | E | 1830 |

Table 5-continued

| Example No. | Compound added | Induction period (minutes) |
|---|---|---|
| 28 | F | 1850 |
| 29 | G | 1800 |
| 30 | H | 1900 |
| 31 | I | 1870 |
| 32 | J | 1800 |
| 33 | K | 1780 |

COMPARATIVE EXAMPLES 37 – 54

The procedures of Examples 23 – 33 were repeated except that conventional anti-deteriorating agents a – q were employed in place of the compounds A – K. In Comparative example 37, no anti-deteriorating agent was added. The results are set forth in Table 6.

Table 6

| Comparative example No. | Anti-detertorating agent | Induction period (minutes) |
|---|---|---|
| 37 | — | 90 |
| 38 | a | 350 |
| 39 | b | 420 |
| 40 | c | 210 |
| 41 | d | 180 |
| 42 | e | 480 |
| 43 | f | 350 |
| 44 | g | 300 |
| 45 | h | 250 |
| 46 | i | 310 |
| 47 | j | 290 |
| 48 | k | 430 |
| 49 | l | 420 |
| 50 | m | 310 |
| 51 | n | 360 |
| 52 | o | 240 |
| 53 | p | 360 |
| 54 | q | 385 |

EXAMPLES 34 – 44

One hundred parts of powdery isotactic polypropylene with no additives (M.I. = 5), 0.03 part of tetrakis[methylene 3-(3,5-di-tert-butyl-4-hydroxyphenyl)propionate]methane, 0.07 part of distearyl 3,3'-thiodipropionate, 0.1 part of 2,6-di-tert-butyl-p-cresol, 0.015 part of calcium stearate and 0.3 part of a compound set out in Table 7 were preliminarily mixed in a mixer. This mixture was placed in a Brabender plastograph adjusted to a rotation speed of 60 r.p.m. and a temperature of 190° C, and kneaded for 8 minutes. The resulting mixture was pressed at 190° C by the use of a spacer to form a film having thickness of 0.5 mm. Between a couple of the so obtained films was placed a copper net of 60 meshes, and this was then pressed at 190° C by the use of a spacer of thickness of 0.8 mm to obtain a copper net buried film. The so obtained film was cut into rectangular (50 mm × 30 mm) pieces which were in turn subjected to the test described below.

The test pieces were suspended in a Gear's oven under an aerial atmosphere at 150° C, and the period at the end of which the pieces deteriorated were determined. The results are set forth in Table 7.

Table 7

| Example No. | Compound added | Period up to deterioration (days) |
|---|---|---|
| 34 | A | 63 |
| 35 | B | 59 |
| 36 | C | 58 |
| 37 | D | 54 |
| 38 | E | 67 |
| 39 | F | 63 |
| 40 | G | 65 |
| 41 | H | 59 |
| 42 | I | 70 |
| 43 | J | 71 |
| 44 | K | 67 |

COMPARATIVE EXAMPLES 55 – 64

The procedures of Examples 34 – 44 were repeated except that some of conventional anti-deteriorating agents a – o are employed in place of the compounds A – K. In Comparative example 55, no anti-deteriorating agent was added. The results are set forth in Table 8.

Table 8

| Comparative example No. | Anti-deteriorating agent | Period up to deterioration (days) |
|---|---|---|
| 55 | — | 3 |
| 56 | a | 10 |
| 57 | c | 9 |
| 58 | d | 3 |
| 59 | e | 38 |
| 60 | g | 10 |
| 61 | h | 10 |
| 62 | k | 34 |
| 63 | n | 18 |
| 64 | o | 10 |

What we claim is:

1. An olefin polymer composition which comprises 100 parts by weight of an olefin polymer and from 0.001 to 5 parts by weight of a compound having the formula

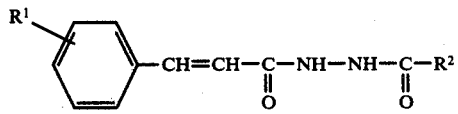

in which $R^1$ represents a hydrogen atom, a halogen atom, a hydroxyl group, an alkyl group having 1 – 3 carbon atoms or an alkoxy group having 1 – 3 carbon atoms, and $R^2$ represents a group of the formula

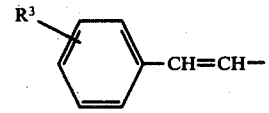

in which $R^3$ represents a hydrogen atom, a hydroxyl group, an alkyl group having 1 – 3 carbon atoms, an alkoxy group having 1 – 3 carbon atoms, a group of the formula

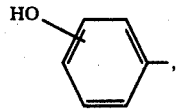

a group of the formula

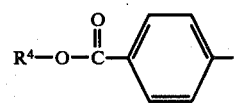

in which R[4] represents an alkyl group having 1 – 3 carbon atoms, or a group of the formula

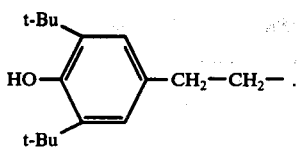

2. A composition as claimed in claim 1 wherein the compound has the formula

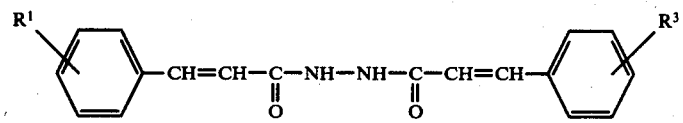

in which R[1] represents a hydrogen atom, a halogen atom, an alkyl group having 1 – 3 carbon atoms or an alkoxy group having 1 – 3 carbon atoms, and R[3] represents a hydrogen atom, an alkyl group having 1 – 3 carbon atoms or an alkoxy group having 1 – 3 carbon atoms.

3. A composition as claimed in claim 2 wherein the compound has the formula

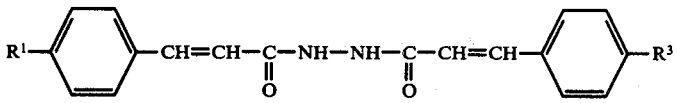

in which R[1] and R[3] are the same or different, and each represents a hydrogen atom, or a methyl or methoxy group.

4. A composition as claimed in claim 1 wherein the compound has the formula

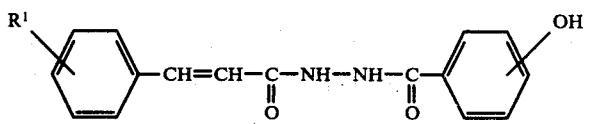

in which R[1] represents a hydrogen atom, a halogen atom, an alkyl group having 1 – 3 carbon atoms or an alkoxy group having 1 – 3 carbon atoms.

5. A composition as claimed in claim 4 wherein the compound has the formula

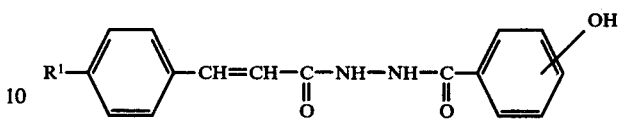

in which R[1] represents a hydrogen atom, or a methyl or methoxy group.

6. A composition as claimed in claim 1 wherein the compound has the formula

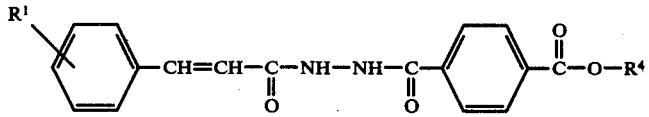

in which R[1] represents a hydrogen atom, a halogen atom, an alkyl group having 1 – 3 carbon atoms or an alkoxy group having 1 – 3 carbon atoms, and R[4] represents an alkyl group having 1 – 3 carbon atoms.

7. A composition as claimed in claim 6 wherein the compound has the formula

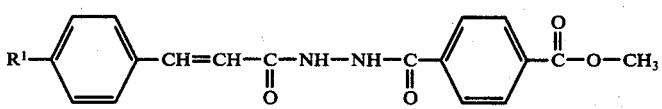

in which R[1] represents a hydrogen atom, or a methyl or methoxy group.

8. A composition as claimed in claim 1 wherein the compound has the formula

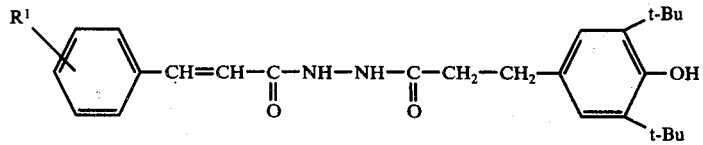

in which R[1] represents a hydrogen atom, a halogen atom, an alkyl group having 1 – 3 carbon atoms or an alkoxy group having 1 – 3 carbon atoms.

9. A composition as claimed in claim 8 wherein the compound has the formula

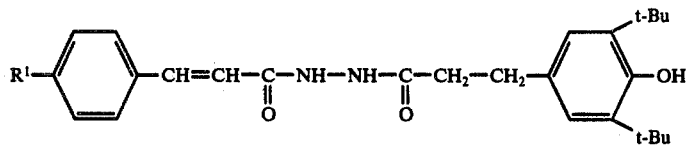

in which R¹ represents a hydrogen or chlorine atom, or a methyl or methoxy group.

10. A composition as claimed in claim 1 wherein the olefin polymer is an ethylene homopolymer, an ethylene — propylene copolymer, isotactic polypropylene or an ethylene — vinyl acetate copolymer.

11. A composition as claimed in claim 1 which comprises 100 parts by weight of an olefin polymer and from a 0.01 to 3 parts by weight of the compound.

12. A composition as claimed in claim 1 which further comprises at least one stabilizing agent, dispersing agent, plasticizer, antistatic agent, filler or pigment.

* * * * *

UNITED STATES PATENT AND TRADEMARK OFFICE
CERTIFICATE OF CORRECTION

PATENT NO. : 4,052,362

DATED : October 4, 1977

INVENTOR(S) : TOSHIO YOSHIKAWA et al

It is certified that error appears in the above-identified patent and that said Letters Patent are hereby corrected as shown below:

Column 2, formula (2): replace "$R^5COCl \rightarrow R^2CONHNHCOR^2$" with ---$R^2COCl \rightarrow R^5CONHNHCOR^2$---.

Column 3, lines 7 and 25, formulae: replace

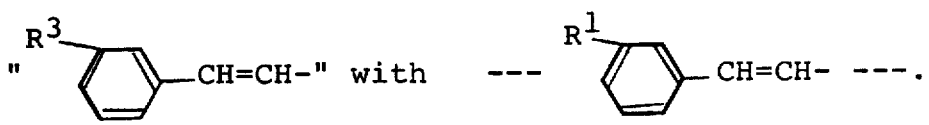

Column 3, line 29: delete "in other words, the above $R^5$".

Column 3, line 58: replace "methylformamide" with ---N-dimethylformamide---.

UNITED STATES PATENT AND TRADEMARK OFFICE
CERTIFICATE OF CORRECTION

PATENT NO. : 4,052,362
DATED : October 4, 1977
INVENTOR(S) : TOSHIO YOSHIKAWA et al It is certified that error appears in the above-identified patent and that said Letters Patent are hereby corrected as shown below:

Column 1, line 40: after "bis[", insert ---β---.

Column 3, lines 48-49: rewrite "hydrogenacarbonate" as ---hydrogencarbonate---.

Column 5, line 12: delete "(VII)" (second occurrence); re-insert ---(VII)--- next to the formula.

Column 7, line 9: rewrite "thiodiporpionates" as ---thiodipropionates---.

Column 7, line 47: rewrite "cnna-" as ---cinna- ---.

Column 10, line 60: rewrite "andi-" as ---anti- ---.

Column 13, line 55: rewrite "Gear's oven" as ---Geer's oven---.

Signed and Sealed this

Eighteenth Day of July 1978

[SEAL]

Attest:

RUTH C. MASON
*Attesting Officer*

DONALD W. BANNER
*Commissioner of Patents and Trademarks*